United States Patent [19]

Parr et al.

[11] Patent Number: 4,801,625

[45] Date of Patent: Jan. 31, 1989

[54] BICYCLIC PHOSPHATE ETHER, ESTER, AND CARBONATE INTUMESCENT FLAME RETARDANT COMPOSITIONS

[75] Inventors: William J. Parr; Arthur G. Mack, both of Naperville; Paul Y. Y. Moy, Des Plaines, all of Ill.

[73] Assignee: AKZO America Inc., New York, N.Y.

[21] Appl. No.: 90,319

[22] Filed: Aug. 27, 1987

[51] Int. Cl.[4] ............................................. C08K 5/52
[52] U.S. Cl. ................................. 523/179; 524/120; 558/74
[58] Field of Search ............... 524/117, 119, 120, 100; 558/74; 521/179

[56] References Cited

U.S. PATENT DOCUMENTS

| | | |
|---|---|---|
| 2,643,261 | 6/1953 | Matuszak et al. ................. 558/74 |
| 3,155,639 | 11/1964 | Emmons et al. ................... 558/74 |
| 3,808,296 | 4/1974 | Brunetti ............................ 558/74 |
| 3,849,522 | 11/1974 | Hills ................................. 558/74 |
| 3,873,496 | 3/1975 | Hills ................................. 524/119 |
| 3,944,633 | 3/1976 | Gresham .......................... 524/119 |
| 4,341,694 | 7/1982 | Halpern ........................... 524/119 |
| 4,454,064 | 6/1984 | Halpern ........................... 558/74 |
| 4,584,331 | 4/1986 | Tamura et al. .................. 524/119 |

FOREIGN PATENT DOCUMENTS 2506207 8/1976 Fed. Rep. of Germany.
889338 2/1962 United Kingdom.

Primary Examiner—Veronica P. Hoke
Attorney, Agent, or Firm—Jeffrey S. Boone

[57] ABSTRACT

A flame resistant composition has (1) an organic polymeric substance (such as polypropylene) in intimate contact with (2) an ether, ester, or carbonate derivative of a bicyclic phosphorous compound (such as pentaerythritol phosphate) and (3) a gas producing compound (such as melamine or ammonium polyphosphate).

41 Claims, No Drawings

BICYCLIC PHOSPHATE ETHER, ESTER, AND CARBONATE INTUMESCENT FLAME RETARDANT COMPOSITIONS

BACKGROUND OF THE INVENTION

This invention relates to flame retardant compounds which may be contacted with organic substances to reduce the tendency of the organic substance to flame. In particular, this invention relates to such flame retardants which act, at least in part, by their ability to intumesce.

For reasons of customer demand, government regulations, and product stewardship, those manufacturing and selling organic substances, particularly synthetic resins, have sought to reduce the tendency of those substances to flame. A suitable flame retardant additive must be economical to purchase, relatively nontoxic, easy to incorporate into the organic substance, nonmigrating, thermally stable, and effective at reducing the tendency of the substance to flame.

The use of flame retardants is not entirely satisfactory in some instances due to the tendency of many such compositions to be toxic, corrosive, or contributors to smoke formation.

One approach toward a workable flame retardant is that of intumescent flame retardants. Organic substances contacted with intumescent flame retardants behave generally as do organic substances contacted with other flame retardants, but upon contact with a flame, they soften, bubble, char, and swell, forming a thick, relatively non-flammable, thermally insulative barrier. Intumescent flame retardants are generally believed to require (a) a polyol component, (b) a dehydration catalyst (eg: phosphoric acid), and (c) a blowing agent. In some instances, a single molecule may provide two or even all three of the components. For instance, pentaerythritol phosphate may be regarded as providing a source of both the polyol component and the dehydration catalyst. In general, intumescent flame retardants are relatively non-toxic, non-corrosive, and low smoke contributors. However, they are also thermally unstable and tend to degrade at the temperature commonly encountered in polymer processing, resulting in discolorization of the polymer.

U.S. Pat. No. 4,454,064 (1984, Borg-Warner, Halpern) teaches the synthesis of pentaerythritol phosphate and its usefulness as an intermediate in the preparation of unnamed flame retardant materials. U.S. Pat. No. 4,341,694 (1982, Borg-Warner, Halpern) teaches the use of pentaerythritol phosphate as an intumescent flame retardant in polymers such as polyolefins. U.S. Pat. No. 3,808,296 (1974, Ciba-Geigy, Brunetti) discloses various hindered phenol esters of pentaerythritol phosphate and their use as "stabilizers" (ie: antioxidants), including such use with a multitude of coaditives including nitrogen-containing basic costabilizers such as melamine. U.S. Pat. No. 4,584,331 teaches the use of various esters and ether derivatives of pentaerythritol phosphate as (non-intumescent) flame retardants for a specific polyphenylene ether composition. U.S. Pat. No. 3,873,496 (1975, FMC, Hills) teaches the use of pentaerythritol phosphate as a non-intumescent flame retardant in polyester. GB 889,338 (1969, Hooker) teaches the synthesis and use of pentaerythritol phosphate as a stabilizer for vinyl halide resins.

SUMMARY OF THE INVENTION

In one respect, the invention is a flame resistant composition having a polymeric substance in contact with (a) an aliphatic ether, ester, or carbonate derivative of pentaeythritol phosphate and (b) a gas producing compound.

Compared to the prior art compositions containing pentaerythritol phosphate, the flame resistant compositions of the invention are particularly thermally stable, resistant to solvent leaching, and non-migrating. In view of the fact that the pentaerythritol phosphate derivatives employed in the invention have less phosphorus (weight percent based on the entire molecule) than does pentaerythritol phosphate, the superior performance of these compositions is particularly surprising.

Cautions

Although this invention concerns "flame retardants", it is important to understand that no compound can render an otherwise flammable composition flame proof. That is, all flammable compositions will under certain conditions burn exothermically despite the incorporation of flame retardants. It is also important to understand that the instant invention has been evaluated only in very small scale laboratory tests. It is not known if this invention is equally as effective under actual fire conditions. Any user of this technology must determine the suitability of its use for each particular application.

DETAILED DESCRIPTION OF THE INVENTION

One component of the invention is a bicyclic phosphorous compound represented by formula I,

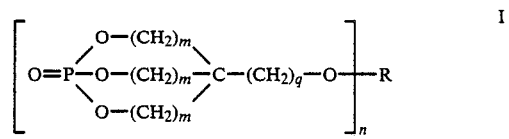

wherein $m=1$ to 3, preferably 1 or 2, more preferably 1; $n-1$ to 3, preferably 1 or 2; $q-1$ to 3, desirably 1 or 2, preferably 1; and R is a $C_1$ to $C_8$, desirably $C_1$ to $C_6$, more desirably $C_1$ to $C_4$, preferably $C_1$ to $C_3$, more preferably $C_1$ or $C_2$ alkyl moiety having a valence of n, such that it completes an ether, ester, or carbonate linkage with the remainder of the molecule. In several preferred embodiments R is $CH_3(CH_2)_a—$, $—(CH_2)_g—$, $CH_3(CH_2)_bC(O—$, $CH(O)—$, $—C(O)$ $(CH_2)_fC(O)—$, $CH_3(CH_2)_dOC(O)—$, $—C(O)O(CH_2)_3OC(O)—$, or $—C(O)—$, wherein $a—0$ to 7, preferably 0 to 2, more preferably 0 or 1, most preferably 0; $b=0$ to 6, preferably 0 to 2, more preferably 0 or 1, most preferably 0; $d=0$ to 6, preferably 0 to 2, more preferably 0 or 1, most preferably 0; $e=1$ to 6, preferably 1 or 2, more preferably 1; $f=0$ to 6, preferably 1 or 2, more preferably 1; and $g=1$ to 7, preferably 1 or 2, more preferably 1.

The bicyclic phosphorous compounds of the invention may be easily prepared by one skilled in the art. The ester version of the bicyclic phosphorous compound may be prepared by the reaction of pentaerythitol phosphate (2,6,7-trioxa-1-phosphabicyclo[2.2.2]octane-4-methanol-1-oxide) with a corresponding carboxylic acid, anhydride, or acid chloride. The carbonate version of the bicyclic phosphorus compound may be prepared by reaction of pentaerythritol phosphate with chloroformate, or carbonyldimidazole followed by reaction with an alcohol. The ether version of the bicyclic phosphorus compound can be prepared by reacting pentaerythritol phosphate with an alkyl halide. The pentaerythritol phosphate starting material may be prepared by the methods taught in aformentioned U.S. Pat. No. 4,341,694, U.S. Pat. No. 3,873,496, and GB No. 889,338, which are incorporated herein by reference.

A second component of the invention is a gas producing compound which is capable of evolving a non-flammable gas upon the application of a flame. Such compounds are generally nitrogen compounds which thermally degrade to yield a nitrogen-containing gas. Such compounds are conventional in intumescent flame retardants and are well known to those skilled in the art. Several such compounds are described in aforementioned U.S. Pat. No. 4,341,694, which is incorporated herein by reference. Desirable gas producing compounds include amines, ureas, guanidines, guanamines, s-triazines, amino acids, and salts thereof. Preferred compounds include ammonium polyphosphate, melamine pyrophosphate, and melamine. Ammonium polyphosphate is a preferred gas producing compound because of its high level of activity and its complementary effect with the bicyclic phosphorous compound (reducing the level of bicyclic phosphorous compound required for a UL 94 rating of V0). Both melamine pyrophosphate and ammonium polyphosphate contain phosphorous which is believed to be released in the form of phosphoric acid. These compounds therefore contribute to the flame retardance by providing a dehydration catalyst as well as acting as a blowing agent. A mixture of gas producing compounds may be used if desired.

A third component of the invention is an organic polymeric substance. Suitable organic polymeric substances must be sufficiently able to swell and bubble to participate in an intumescent formation. In general, suitable organic polymeric substances will be synthetic polymers. Suitable synthetic polymers include polyolefins such as polypropylene (especially including polypropylene copolymers containing, for instance, up to 20% comonomer such as polyethylene), polybutylene, and EPDM (ethylene propylene dimer); polyesters such as polybutyleneterephthalate and polyethyleneterephthalate; polyamides such as nylon 6; polycarbonates; ABS (acrylonitrile-butadiene-styrene); polyvinylaromatics such as polystyrene; polyacrylates such as polymethylmethacrylate; polyurethanes; and polyphenylene oxides. Preferred polymers are polyolefins, polyesters and polyamides. More preferred are polyolefins and polyesters. Still more preferred are polyolefins, and most preferred is polypropylene (including copolymers thereof).

The invention requires that the bicyclic phosphorous compound and the gas producing compound (the flame retardant compounds) be intimately contacted with the organic substance. By "intimately contacted" is meant that the flame retardant compounds and the organic substance all be finely divided and uniformly distributed. This is, of course, a matter of degree, and any degree of contact which improves the flame resistance properties of the organic substance is acceptable. Further, the nature of "finely divided" and "uniformly distributed" will vary according to the nature of the organic substance. Obviously, an insoluble polymer which is highly filled with a coarse filler will allow for less uniform distribution than an unfilled polymer which can be solution blended with the flame retardant compounds. A particular advantage of many compounds of the invention is that they have melting points below that used to melt blend most polymers, which permits more even dispersion of the compounds in the organic substances.

The flame retardant compounds are incorporated into the organic substance in a flame retarding amount. By "flame retarding amount" is meant an amount which will render the organic substance more flame resistant than if the flame retardant compound were totally absent. Although the precise amount of the flame retardant compounds which are most advantageously added to the organic substance will vary with the particular flame retardants, the particular organic substance, and the degree of intimate contact, generally the bicyclic phosphorous compound will be present in a char producing amount and the gas producing compound will be present in a bubble producing amount. By "char producing amount" is meant on amount sufficient to, in combination with the gas producing compound, produce a relatively non-flammable insulating layer of char on the surface of the organic substance when exposed to a flame. By "bubble producing amount" is meant an amount sufficient, in combination with the bicyclic phosphorous compound, to produce sufficient gas to expand the organic substance to produce a thermally insulating foam-type structure. Generally, the bicyclic phosphorous compound will be present at 5 to 50, preferably 10 to 40, and more preferably 12 to 30 weight percent based on the weight of the organic substance including all additives. Generally, the gas producing compound will be present at 1 to 30, preferably 3 to 25, and more preferably 4 to 20 weight percent based on the weight of the organic substance including all additives. For any given combination of bicyclic phosphorous compound and gas producing compound there will be an optimum ratio for achieving the best flame retardancy. This optimum ratio can easily be determined by simple trials.

The invention is further described in the following examples.

EXAMPLE I 2,6,7-Trioxa-1-phosphabicylo[2.2.2]octane-4-methanol-1-oxide (45 g, 0.25 mole) and acetic anhydride (100 g, 1 mole) were charged to a 500 ml reactor and heated at reflux for one hour. After cooling the excess acetic anhydride and by-product acetic acid were largely removed by evaporation under reduced pressure to leave a sticky white solid. This solid was recrystallized from dichloromethane and hexane, followed by drying in a fluidized bed at 100° C., to give 47.2 g of white crystals having a melting point of 170°–172° C. Carbon-13 and phosphorous-31 NMR spectroscopy confirmed this material to be the desired acetate (Compound A, R=$CH_3C(O0-)$).

EXAMPLE II 2,6,7-Trioxa-1-phosphabicyclo[2.2.2]octane-4-methanol-1-oxide (180 g, 1 mole) and 96% formic acid (280 g) were charged to a one liter reactor. Concentrated hydrochloric acid (10 drops) was added and the mixture heated under reflux for six hours. Excess formic acid was then removed under reduced pressure by distillation, leaving 227 g of a white solid. This material was subjected to column chromatography on silica using 9:1 v/v dichloromethane-methanol as eluent, followed by recrystallization from dichloromethane, methanol and diethyl ether to afford a white solid having a melting point of 164°–165° C. The structure was confirmed by IR and NMR spectroscopy to correspond to that of the desired formate (Compound B, R=HC(O)—).

EXAMPLE III 2,6,7-Trioxa-1-phosphabicyclo[2.2.2]octane-4-methanol-1-oxide (90 g, 0.5 mole), triethylamine (50.5 g, 0.5 mole), and acetonitrile (300 ml) were charged to a one liter reactor and stirred while propionyl chloride (69.4 g, 0.75 mole) was added dropwise over 20 minutes. An exothermic reaction occurred and after first becoming clear a precipitate formed. Stirring was continued for four hours and then the precipitated triethylamine hydrochloride removed by filtration. Solvent was evaporated from the filtrate to leave a sticky solid. This solid was dissolved in dichloromethane and the solution washed (2×300 ml) with water, dried over MgSO$_4$, filtered, and the solvent evaporated to afford 105 g of solid. This was subjected to charcoal treatment followed by recrystallization from chloform and diethyl ether. A white solid (77 g) of melting point 96°–97° C. was obtained which was shown by NMR and IR spectroscopy to be the desired propionate. (Compound C, R=CH$_3$CH$_2$C(O)—).

In a similar manner the following esters of 2,6,7-trioxa-1-phosphabicyclo[2.2.2]octane-4-methanol-1-oxide were prepared from the corresponding acid chlorides:

| Ester | Melting Point (°C.) | Identification |
| --- | --- | --- |
| Benzoic | 236–238 | Compound D*, R = C$_6$H$_5$C(O)— |
| Adipic | 232–235 | Compound E, R = —(O)C(CH$_2$)$_4$C(O) |
| Succinic | 218–220 | Compound F, R = —(O)C(CH$_2$)$_2$C(O)— |

*Not an example of the invention

EXAMPLE IV 2,6,7-Trioxa-1-phosphabicyclo[2.2.2]octane-4-methanol-1-oxide (90 g, 0.5 mole), pyridine (39.5 g, 0.5 mole) and acetonitrile were charged to a one liter reactor and stirred while methyl chloroformate (64 g) was added dropwise. An exothermic reaction to 60° C. occurred and a clear solution resulted. Additional quantities of methyl chloroformate (22 g, 60 g, 30 g) were added at intervals over a total reaction time of 30 h (disappearance of starting material monitored by TLC). The solvent was evaporated to afford 161 g of a brown, viscous oil which was subjected to column chromatography on silica gel using dichloromethane as eluent. This gave 36 g of a white solid which was further purified by recrystallization from dichloromethane and diethyl ether to afford 32 g of white solid having a melting point of 148°–150° C., which NMR and IR spectroscopy confirmed to be the methyl carbonate derivative. (Compound G, R=CH$_3$OC(O)—). [The inefficient utilization of methyl chloroformate in this reaction indicates side-reactions to be occurring].

EXAMPLE V 2,6,7-Trioxa-1-phosphabicyclo[2.2.2]octane-4-methanol-1-oxide (90 g, 0.5 mole) and 300 ml of acetonitrile were stired in a one liter vessel under a nitrogen atmosphere. Carbonyl diimidazole (81 g, 0.5 mole) was added portionwise over five minutes (gas was evolved). After stirring at ambient temperature for 30 minutes, ethanol (100 g) was added, followed by a small amount of potassium t-butoxide. The reaction was heated to reflux for two hours, cooled, and the solvent evaporated to leave a viscous yellow oil. This was dissolved in dichloromethane and the solution washed well with water, dried over MgSO$_4$, filtered, and the filtrate evaporated to afford 90.5 g of a white solid. This material was subjected to column chromatography on silica gel using a 9:1 v/v mixture of dichloromethane:methanol as eluent. Recovered solid was recrystallized from dichloromethane and diethyl ether to give a white solid having a melting point of 132°–134° C., which NMR and IR spectroscopy confirmed to be the desired ethyl carbonate derivative. (Compound H, R=CH$_3$CH$_2$OC(O)—).

By similar procedures the following carbonates of 2,6,7-trioxa-1-ohosphabicyclo[2.2.2]octane-4-methanol-1-oxide were also prepared:

| Carbonate | Melting Point (°C.) | Identification |
| --- | --- | --- |
| butyl | 81–83 | Compound J, R = CH$_3$(CH$_2$)$_3$OC(O)— |
| bis | 320 (decomposed) | Compound K, R = —C(O)— |

EXAMPLE Va 2,6,7-Trioxa-1-phosphabicyclo[2.2.2]octane-1-methanol-1-oxide (89 g; 0.5 mole), powdered potassium hydroxide (28.2 g, 0.5 mole) and dimeethylsulfoxide (DMSO) (500 ml) were charged into a 1 liter flask. Methyl iodide (107 g; 0.75 mole) was added dropwise over 1 hour. An exothemic reaction resulted and the reaction turned brown. The mixture was stirred for 4 hours and the DMSO was then removed by distillation to leave a dark brown oil. Column chromatography on silica eluting with 9:1 dichloromethane:methanol followed by recrystallization from dichloromethane and ether gave 25 g of white crystals having a melting point of 131°–132° C. The structure of this methyl ether derivative (Compound L, R=CH$_3$—) was confirmed by $^{13}$C and $^{31}$P NMR.

EXAMPLE VI

Polypropylene was melt blended with various additives in the proportions shown in Table 1 by mixing in a Haake twin-rotor internal bowl mixer operating at 165°–180° C. After mixing for five minutes the formulations were removed from the mixer and compression moulded between chromed steel plates at 190° C. to give 1/16″ (1.6 mm). Specimens were cut from these sheets and subjected to the Underwriters Laboratory UL94 vertical burn test to assess flammability. In the UL94 test the ratings, from best to worst, are V0, V1, V2 and F. The results are shown in Table 1.

From Table 1 it will be seen that neither 2,6,7-Trioxa-1-phosphabicyclo[2.2.2]octane-4-methanol-1-oxide (Pentaerythritol phosphate, Compound X, R=H [not an sample of the invention]) nor the acetate thereof, (Compound A), are able to impart a V0 rating to polypropylene alone, even at 30% loading. Similarly ammonium polyphosphate, melamine pyrophosphate, and melamine alone are ineffective at flame retarding polypropylene. Both X and A, however, exhibit a synergism, with respect to imparting a V0 rating to polypropylene, with ammonium polyphosphate, melamine pyrophosphate and melamine. The optimum ratio of X or A to synergist varies for each particular synergist (see Table 1) but, in general, the total weight loading of X or A and synergist must be above 24% to result in a V0 rating. The synergist will always contain nitrogen atoms (eg melamine) but may also contain phosphorus and oxygen atoms (melamine pyrophosphate, ammonium polyphosphate). In addition, mixtures of synergists may also be used effectively. It should be noted that Compound A of the present invention imparts V0 ratings to polypropylene at similar, or slightly lower, loadings than Compound X of U.S. Pat. 4,341,694, both both are used with an appropriate synergist. This is surprising in that the acetate contains a lower phosphorus content than Compound X (13.96% versus 17.2% P) so that one might expect a higher loading of acetate than X to be required.

EXAMPLE VII

Polypropylene was compounded and assessed for UL94 flammability rating as described in Example VI using a variety of ester and carbonate analogues of Compound A. Formulations and results are shown in Table 2. It can be seen that as the number of carbon atoms in the ester function increases, the relative ability of the additive to impart a V0 rating to polypropylene decreases. Highest activity is thus observed for the formate (Compound B). This is reasonable since the percentage phosphorus and oxygen in the additive decreases with increasing carbon content. Table 2 also illustrartes not only that ester derivatives of Compound X, but also carbonic acid esters, are capable of imparting a V0 rating to polypropylen when used in conjunction with a suitable synergist; highest activity is observed when the number of carbon atoms is minimized. When the methyl carbonate (Compound G) was heated alone on a spatula with a flame a large amount of foam and char was produced (i.e. intumescent behaviour); however, this carbonate did not impart a V0 rating to polypropylene in the absence of a synergist. Ether derivatives of Compound X, such as Compound L, are also able to impart V0 ratings to polypropylene when used with synergists.

EXAMPLE VIII

Various grades of polypropylene homopolymer and co-polymer were processed as described in Example VI, according to the formulations given in Table 3. The UL94 results contained in Table 3 demonstrate that Compound A of the present invention when used at 12% by weight with 18% ammonium polyphosphonate is capable of imparting V0 ratings to polypropylene homopolymers of widely varying melt flow indices, and also to polypropylene co-polymers.

EXAMPLE IX

Polypropylene formulations were prepared according to the proportions set out in Table 4 and processed into 1/16" (1.6 mm) thick sheets as described in Example VI. One set of specimens from each formulation was evaluated in the UL94 test. Two further sets of specimens were cut for each formulation and placed in the thimble of a soxhlet extraction apparatus, deionized water was used as the extraction medium. One set of specimens was extracted for 48 hours and the second set for 100 hours. Each set of specimens was dried and the weight loss was recorded. Results are shown in Table 4. It will be noted that the amount of weight lost after water extraction is less for the formulations containing Compounds A or G of the present invention than for the formulation containing the prior art compound X.

EXAMPLE X

The volatility/thermal stability of several of the intumescent type flame retardant additives herein considered was examined by thermogravimetric analysis using a temperature rise rate of 20° C./minute and a nitrogen flow rate of 20 ml/minute. Results are shown in Table 5. First it can be noted that the compounds of the present invention exhibit lower weight losses than the commercial intumescent flame retardant C329. The acetate and especially the formate, esters possess improved thermal stability/reduced volatility compared to the prior art Compound X. Intumescent flame retardants of improved thermal stability compared to existing materials are highly desirable since they allow a greater latitude in compounding temperatures to be exercised.

EXAMPLE XI

Polypropylene polymer was dry blended with either Compound X and APP (13%+17%) or Compound A and APP (12%+18%) and added to a Haake twin-screw extruder operating with barrel/die temperatures of 190°–220° C. The extrudates were dried and injection moulded in a Newbury 50 ton machine operating with barrel/die temperatures of 225°–245° C. The resulting specimens were compared to polypropylene containing no additives for tensile strength and Vicat softening point. The specimens containing the Compound A of the present invention retained 83% of the original tensile strength and a Vicat Softening point of 146° C. (147° C. for virgin polypropylene). The formulation containing the prior out compound X possessed a lower Vicat softening point (142° C.) and retained less of the original tensile strength (79.7%). Moreover the lesser thermal stability of the prior art compound X compared to Compound A of the present invention was manifested in the colour of the specimens obtained in the above injection moulding; the surface of the specimens containing Compound X exhibited brown streaks, while the specimens containing Compound A were not discolored. These data are reported in Table 8.

EXAMPLE XII

Polypropylene specimens produced as in Example XI by extrusion/injection moulding containing Compound X, Compound A, or the commercial additive Charguard C329 were placed in an Atlas weatherometer and subjected to alternating periods of UV irradiation and humidity for 304 hours. The samples were then assessed for blooming of the additives to the surface of the specimen (blooming is generally considered to be an undesirable feature in a flame retardant additive). The results are shown in Table 6 and clearly demonstrate that Compound A of the present invention is much superior to the prior art compound X with respect to blooming.

EXAMPLE XIII

Polybutylene (Shell DP8510) was melt blended with additives in the proportions shown in Table 7 by mixing in a Haake twin-rotor internal bowl mixer operating at 110°–120° C. After mixing five minutes, the formulations were removed and compression moulded into sheets of 1/16" (1.6 mm) thickness. Specimens cut from these sheets were assessed for flammability by the UL94 vertical burn test. Results are shown in Table 7; it can be seen that Compound A of the present invention imparts V0 ratings to polybutylene when used in conjunction with a suitable synergist.

EXAMPLE XIV

Polybutylene terephthalate (General Electric Valox 420) containing 30% by weight of glass fiber was melt blended with additives, in the proportions shown in Table 7, by mixing in a Haake twin-rotor internal bowl mixer at 225° C. for 5 minutes. The formulations were removed and compression moulded to 1/16" (1.6 mm) thickness at 235° C. Specimens cut from these sheets were assessed for flammability by the UL94 vertical burn test. The results are shown in Table 7 and demonstrate that compounds of the present invention can impart V0 ratings to polyester polymers. Inclusion of the flame retarding additives caused no discoloration of the polymer.

TABLE 1

| Formulation No. | Fire Rating Weight %[1] | | | | | | UL 94 Rating 1/16" thickness |
|---|---|---|---|---|---|---|---|
| | PP | Compound X | Compound A | APP | Melamine | MPP | |
| 1 | 100 | — | — | — | — | — | F |
| 2 | 70 | — | — | 30 | — | — | V2 |
| 3 | 70 | — | — | — | 30 | — | F |
| 4 | 70 | — | — | — | — | 30 | V2 |
| 5 | 70 | 30 | — | — | — | — | F |
| 6 | 70 | — | 30 | — | — | — | F |
| 7 | 75 | — | 10 | 15 | — | — | F |
| 8 | 70 | — | 10 | 20 | — | — | F |
| 9 | 72 | — | 12 | 16 | — | — | V2 |
| 10 | 71 | — | 12 | 17 | — | — | V0 |
| 11 | 70 | — | 12 | 18 | — | — | V0 |
| 12 | 70 | — | 15 | 15 | — | — | V0 |
| 13 | 70 | — | 18 | 12 | — | — | V0 |
| 14 | 75 | 10 | — | 15 | — | — | F |
| 15 | 70 | 10 | — | 20 | — | — | V2 |
| 16 | 68 | 12 | — | 20 | — | — | V1 |
| 17 | 70 | 13 | — | 17 | — | — | V0 |
| 18 | 70 | 15 | — | 15 | — | — | V0 |
| 19 | 70 | 18 | — | 12 | — | — | V0 |
| 20 | 76 | — | 18 | — | 6 | — | F |
| 21 | 73 | — | 18 | — | 9 | — | F |
| 22 | 70 | — | 18 | — | 12 | — | F |
| 23 | 70 | — | 20 | — | 10 | — | F |
| 24 | 70 | — | 15 | — | 15 | — | F |
| 25 | 70 | — | 12 | — | 18 | — | F |
| 26 | 70 | — | 22 | — | 8 | — | V2/F |
| 27 | 70 | — | 24 | — | 6 | — | V0 |
| 28 | 70 | — | 26 | — | 4 | — | V0 |
| 29 | 76 | 18 | — | — | 6 | — | F |
| 30 | 73 | 18 | — | — | 9 | — | F |
| 31 | 70 | 18 | — | — | 12 | — | F |
| 32 | 70 | 15 | — | — | 15 | — | F |
| 33 | 70 | 22 | — | — | 8 | — | V0 |
| 34 | 70 | 24 | — | — | 6 | — | V0 |
| 35 | 70 | 26 | — | — | 4 | — | V0 |
| 36 | 76 | — | 18 | — | — | 6 | V0/F |
| 37 | 73 | — | 18 | — | — | 9 | V0 |
| 38 | 70 | — | 18 | — | — | 12 | V0 |
| 39 | 70 | — | 15 | — | — | 15 | V0 |
| 40 | 70 | — | 12 | — | — | 18 | V0 |
| 41 | 80 | — | 16 | — | — | 4 | F |
| 42 | 78 | — | 16 | — | — | 6 | V1 |
| 43 | 76 | — | 16 | — | — | 8 | V0 |
| 44 | 76 | 18 | — | — | — | 6 | V2 |
| 45 | 73 | 18 | — | — | — | 9 | V0 |
| 46 | 70 | 18 | — | — | — | 12 | V0 |
| 47 | 70 | 15 | — | — | — | 15 | V0 |
| 48 | 70 | 12 | — | — | — | 18 | V0 |
| 49 | 80 | 16 | — | — | — | 4 | V2 |
| 50 | 76 | 16 | — | — | — | 8 | V2 |
| 51 | 70 | — | 12 | — | 3 | 15 | V0 |
| 52 | 70 | — | 12 | — | 6 | 12 | V0/F |
| 53 | 70 | — | 12 | — | 9 | 9 | F |
| 54 | 70 | — | 12 | 15 | 3 | — | V0 |
| 55 | 70 | — | 12 | 12 | 6 | — | V0 |
| 56 | 70 | — | 12 | 9 | 9 | — | V0 |

[1]PP = polypropylene
For Compound X, R = H (Not an example of the invention).
For Compound A, R = CH3C(O)—.
APP = Ammonium polyphosphate (Phoschek P30-Monsanto).
MPP = Melamine pyrophosphate (White Chem. Co.).

TABLE 2

| | Fire Rating Formulation No. | | | | | | | | | | | | | | | | | | | | | | | | |
|---|---|---|---|---|---|---|---|---|---|---|---|---|---|---|---|---|---|---|---|---|---|---|---|---|---|
| | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
| % PP | 70 | 73 | 73 | 71.5 | 70 | 70 | 70 | 70 | 70 | 70 | 68 | 70 | 70 | 70 | 70 | 70 | 70 | 70 | 70 | 70 | 67 | 70 | 70 | 67 | 70 |

TABLE 2-continued

Fire Rating

| Formulation No. | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|---|
| % APP | 18 | 15 | 18 | 18 | 18 | 18 | 17 | 17 | 18 | 17 | 19 | 18 | — | 18 | 15 | 12 | — | 18 | 12 | 17 | 18 | — | 17 | 18 | 18 |
| % Compound B |  | 12 | 9 | 10.5 | 12 |  |  |  |  |  |  |  |  |  |  |  |  |  |  |  |  |  |  |  |  |
| % Compound A | 12 |  |  |  |  |  |  |  |  |  |  |  |  |  |  |  |  |  |  |  |  |  |  |  |  |
| % Compound C |  |  |  |  |  | 12 | 13 |  |  |  |  |  |  |  |  |  |  |  |  |  |  |  |  |  |  |
| % Compound D |  |  |  |  |  |  |  | 13 | 15 |  |  |  |  |  |  |  |  |  |  |  |  |  |  |  |  |
| % Compound E |  |  |  |  |  |  |  |  |  | 13 | 13 |  |  |  |  |  |  |  |  |  |  |  |  |  |  |
| % Compound F |  |  |  |  |  |  |  |  |  |  |  | 12 |  |  |  |  |  |  |  |  |  |  |  |  |  |
| % Compound G |  |  |  |  |  |  |  |  |  |  |  |  | 30 | 12 | 15 | 18 |  |  |  |  |  |  |  |  |  |
| % Compound H |  |  |  |  |  |  |  |  |  |  |  |  |  |  |  |  | 30 | 12 | 18 |  |  |  |  |  |  |
| % Compound J |  |  |  |  |  |  |  |  |  |  |  |  |  |  |  |  |  |  |  | 13 | 15 |  |  |  |  |
| % Compound K |  |  |  |  |  |  |  |  |  |  |  |  |  |  |  |  |  |  |  |  |  | 30 | 13 | 15 |  |
| % Compound L |  |  |  |  |  |  |  |  |  |  |  |  |  |  |  |  |  |  |  |  |  |  |  |  | 12 |
| UL 94 Rating at 1/16" thickness | V0 | V0 | F | V0 | V0 | V0/F | V0 | F | F | F | V2 | F | F | V0 | V0 | V0 | F | F | F/V2 | F | F | F | V2 | V0 | V0 |

TABLE 3

Fire Rating and Melt Viscosity

| Sample | Manufacturer and Grade of Polypropylene | Type | Melt Flow Index (g/10 min) | UL 94 Rating at 1/16" For Formulation Containing 12% Compound A and 18% APP |
|---|---|---|---|---|
| 3-1 | Shell HY6100 | Homopolymer | 1.5 | V0 |
| 3-2 | Himont PD195 | Homopolymer | 1.5 | V0 |
| 3-3 | Phillips Marlex HGZ08002 | Homopolymer | 8 | V0 |
| 3-4 | Himont PD701 | Homopolymer | 35 | V0 |
| 3-5 | Shell PDC 1080 | Copolymer | 5 | V0 |

TABLE 4

Solvent Extraction

| | Sample | | |
|---|---|---|---|
| | 4-1 | 4-2 | 4-3 |
| % PP | 70 | 70 | 70 |
| % APP | 17 | 18 | 18 |
| % Compound X* | 13 | — | — |
| % Compound A | — | 12 | — |
| % Compound G | — | — | 12 |
| UL 94 Rating at 1/16" Unextracted | V0 | V0 | V0 |
| % Wt. loss 48 h | 5.3 | 2.4 | 1.2 |
| % Wt. loss 100 h | 7.2 | 3.0 | 2.4 |

*Not a compound of the present invention

TABLE 5

Thermal Stability

| | | Temp (°C.) for a Wt. Loss of | | | |
|---|---|---|---|---|---|
| Sample | Compound | 1% | 2% | 5% | 10% |
| 5-1 | Charguard C329*[(1)] | 100° | 230° | 310° | 335° |
| 5-2 | Compound X* | 100° | 295° | 310° | 320° |
| 5-3 | Compound A | 170° | 310° | 360° | >380° |
| 5-4 | Compound B | 250° | 340° | >360° | |
| 5-5 | Compound G | 150° | 240° | 290° | 315° |

*Not an example of the invention
[(1)]Great Lakes Chem. Corp. Structure is:

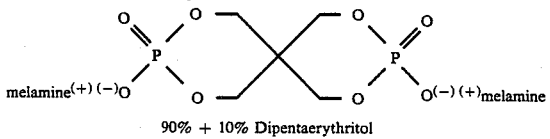

90% + 10% Dipentaerythritol

TABLE 6

Weather Test

| | Sample | | |
|---|---|---|---|
| | 6-1 | 6-2 | 6-3 |
| % PP | 70 | 70 | 70 |
| % Compound X* | 13 | — | — |
| % Compound A | — | 12 | — |

TABLE 6-continued

Weather Test

| | Sample | | |
|---|---|---|---|
| | 6-1 | 6-2 | 6-3 |
| % Charguard C329* | — | — | 30 |
| % APP | 17 | 18 | — |
| Bloom after 304 hrs in Atlas Weatherometer | Heavy | Light | Light/Moderate |

*Not an example of the invention

TABLE 7

Fire Rating

| | Sample | | | | | | |
|---|---|---|---|---|---|---|---|
| | 7-1 | 7-2 | 7-3 | 7-4 | 7-5 | 7-6 | 7-7 |
| % Polybutylene | 73 | 70 | 70 | 70 | — | — | — |
| % PBT* | — | — | — | — | 70 | 70 | 70 |
| % Compound A | 18 | 18 | 15 | 12 | 18 | 15 | 12 |
| % APP | 9 | 12 | 15 | 18 | 12 | 15 | 18 |
| UL 94 Rating at 1/16" thickness | V2 | V0 | V0 | V0 | V2 | V0 | V0 |

*Containing 30% glass fiber

TABLE 8

Physical Performance

| Sample | Additive | % Tensile Strength Retained | Loss of Vicat (°C.) | Discoloration |
|---|---|---|---|---|
| 8-1 | Compound A | 83.0 | 1 | None |
| 8-2 | Compound X* | 79.7 | 5 | Brown streaks |

*Not an example of the invention

SUMMARY OF EXAMPLES

The foregoing data demonstrate the utility and unexpected results of the present invention. Specifically, the data show that the compositions of the invention are as effective or more effective than the compositions of the prior art containing pentaerythritol phosphate. The data further show that the compositions of the invention are more thermally stable and more resistant to solvent extraction, weather degradation, discolorization, loss of tensible strength, and loss of viscat softening point, than the prior art compositions employing pentaerythritol phosphate.

We claim:

1. A flame resistant composition comprising an organic polymeric substance having in intimate contact therewith, (a) a char producing amount of a bicyclic phosphorous compound of the formula

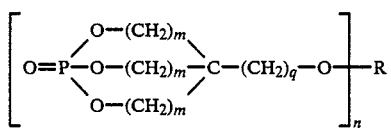

wherein $m=1$ to 3; $n=1$ to 3; $q=1$ to 3; and R is a $C_1$ to $C_8$ aliphatic moiety having a valence of n, such that R completes either an ether, carboxylic acid, ester, or carbonate linkage with the remainder of the molecule; and (b) a bubble producing amount of a gas producing compound which releases a non-flammable gas upon application of a flame.

2. The composition of claim 1 wherein $m=1$.
3. The composition of claim 1 wherein $n=1$.
4. The composition of claim 1 wherein $q=1$.
5. The composition of claim 1 wherein $m=1$, $n=1$, and $q=1$.
6. The composition of claim 1 wherein R is such that it completes an ether linkage.
7. The composition of claim 6 wherein R is $CH_3(CH_2)_a$— or —$(CH_2)_g$—, wherein $a=0$ to 7 and $g=1$ to 7.
8. The composition of claim 7 wherein $a=0$ to 2 and $g=1$ or 2.
9. The composition of claim 8 wherein $a=0$ or 1 and $g=1$.
10. The composition of claim 9 wherein $R=CH_3$—.
11. The composition of claim 1 wherein R is such that it completes an ester linkage.
12. The composition of claim 11 wherein R is $CH_3(CH_2)_bC(O)$—, —$C(O)(CH_2)_fC(O)$— or $CH(O)$—, wherein $b=0$ to 6 and $f=0$ to 6.
13. The composition of claim 12 wherein $b=0$ to 2 and $f=1$ or 2.
14. The composition of claim 12 wherein $b=0$ or 1 and $f-1$.
15. The composition of claim 14 wherein R is $CH_3C(O)$— or $CH(O)$—.
16. The composition of claim 15 wherein R is $CH(O)$—.
17. The composition of claim 1 wherein R is such that it completes a carbonate linkage.

18. The composition of claim 17 wherein R is $CH_3(CH_2)_dOC(O)$—, —$C(O)O(CH_2)_3OC(O)$—, or —$C(O)$—, wherein $d=0$ to 6 and $e=1$ to 6.
19. The composition of claim 18 wherein $d=0$ to 2 and $e=1$ or 2.
20. The composition of claim 19 wherein $d=0$ or 1 and $e=1$.
21. The composition of claim 20 wherein R is $CH_3OC(O)$ or —$OC(O)$—.
22. The composition of claim 21 wherein R is $CH_3OC(O)$.
23. The composition of claim 1 wherein the gas producing compound is a nitrogen compound which thermally decomposes.
24. The composition of claim 23 wherein the nitrogen compound is an amine, urea, guanidine, guanamine, s-triazine, amino acid, or salts thereof.
25. The composition of claim 24 wherein the nitrogen compound is melamine, melamine pyrophosphate, or ammonium polyphosphate.
26. The composition of claim 25 wherein the nitrogen compound is melamine.
27. The composition of claim 25 wherein the nitrogen compound is melamine pyrophosphate.
28. The composition of claim 25 wherein the nitrogen compound is ammonium polyphosphate.
29. The composition of claim 1 wherein the organic polymeric substance is a synthetic polymer.
30. The composition of claim 26 wherein the synthetic polymer is a polyolefin, polyester, polyamide, ABS, polyvinylaromatic, polyacrylate, polyurethane, or polyphenylene oxide.
31. The composition of claim 30 wherein the synthetic polymer is a polyolefin, polyester, or polyamide.
32. The composition of claim 31 wherein the synthetic polymer is a polyolefin or polyester.
33. The composition of claim 32 wherein the synthetic polymer is a polyolefin.
34. The composition of claim 33 wherein the polyolefin is a polypropylene.
35. The composition of claim 32 wherein the synthetic polymer is a polyester.
36. The composition of claim 1 wherein the bicyclic phosphorous compound is present at 5 to 50 weight percent, based on the weight of the composition.
37. The composition of claim 36 wherein the bicyclic phosphorous compound is present at 10 to 40 weight percent, based on the weight of the composition.
38. The composition of claim 37 wherein the bicyclic phosphorous compound is present at 12 to 30 weight percent, based on the weight of the composition.
39. The composition of claim 1 wherein the gas producing compound is present at 1 to 30 weight percent, based on the weight of the composition.
40. The composition of claim 39 wherein the gas producing compound is present at 3 to 25 weight percent, based on the weight of the composition.
41. The composition of claim 40 wherein the gas producing compound is present at 4 to 20 weight percent, based on the weight of the composition.

* * * * *